(12) United States Patent
Fujita et al.

(10) Patent No.: US 6,245,029 B1
(45) Date of Patent: Jun. 12, 2001

(54) STYLET AND CONNECTOR THEREFOR

(75) Inventors: Nozomu Fujita; Hajime Tsujikawa, both of Ohtsu (JP)

(73) Assignee: Nissho Corporation, Osaka (JP)

( * ) Notice: Subject to any disclaimer, the term of this patent is extended or adjusted under 35 U.S.C. 154(b) by 357 days.

(21) Appl. No.: 08/868,536

(22) Filed: Jun. 4, 1997

Related U.S. Application Data

(63) Continuation of application No. 08/600,046, filed on Feb. 12, 1996, now abandoned.

(30) Foreign Application Priority Data

Feb. 21, 1995 (JP) ..................................................... 7-032542

(51) Int. Cl.⁷ ..................................................... A61B 5/00
(52) U.S. Cl. ................... 600/585; 604/170.02; 604/533; 604/164.07
(58) Field of Search ..................................... 604/280, 282, 604/264, 283, 164–5, 170, 267, 905, 164.07 170.02, 533, 539; 128/654, 656–8, 772; 600/433.5, 585

(56) References Cited

U.S. PATENT DOCUMENTS

| | | |
|---|---|---|
| Re. 33,911 * 5/1992 | Samson et al. | ........................ 604/164 |
| 4,388,076 6/1983 | Waters . | |
| 4,496,347 1/1985 | MacLean et al. . | |
| 4,559,046 * 12/1985 | Groshong et al. | ..................... 604/170 |
| 4,571,239 2/1986 | Heyman . | |
| 4,636,200 1/1987 | Vaillancourt . | |
| 5,011,478 * 4/1991 | Cope | ..................................... 604/170 |
| 5,226,427 * 7/1993 | Buckberg et al. | ..................... 604/170 |
| 5,231,989 * 8/1993 | Middleman et al. | ................. 604/280 |
| 5,257,620 11/1993 | Schermerhorn . | |
| 5,295,968 3/1994 | Martel et al. . | |
| 5,382,238 * 1/1995 | Abrahamson et al. | ............... 604/170 |
| 5,492,532 * 2/1996 | Ryan et al. | ........................... 604/283 |
| 5,498,249 * 3/1996 | Quinn | .................................... 604/280 |
| 5,509,912 * 4/1996 | Vaillancourt et al. | .................. 604/88 |
| 5,536,258 * 7/1996 | Folden | .................................. 604/265 |
| 5,549,554 * 8/1996 | Miraki | .................................. 604/283 |
| 5,584,812 * 12/1996 | Martin | .................................. 604/164 |

* cited by examiner

Primary Examiner—Richard K. Seidel
Assistant Examiner—Michael M Thompson
(74) Attorney, Agent, or Firm—Birch, Stewart, Kolasch & Birch, LLP

(57) ABSTRACT

A stylet which comprises a stylet assembly body and a connector for connecting the stylet to a catheter. The stylet body has a piece of wire bent double and twisted together to form a rounded end serving as a distal end at one end. The connector has a stylet connecting part for holding a proximal end of the stylet body. The connector also holds the catheter to prevent the catheter from slipping from the stylet during use.

8 Claims, 6 Drawing Sheets

STYLET AND CONNECTOR THEREFOR

This application is a continuation, of application Ser. No. 08/600,046 filed on Feb. 12, 1996, now abandoned.

BACKGROUND OF THE INVENTION

1. Field of the Invention

The present invention relates to a stylet assembly including a stylet, or stylet body, used for insertion of a catheter into the blood vessel and to a connector for holding a stylet and connecting it to a catheter. More particularly, it relates to a stylet to be inserted into a lumen of a venous catheter for total parenteral nutrition to give a desired rigidity to the catheter and to a connector for holding the stylet in the lumen thereof, which makes it possible to allow a medical solution to flow into the catheter through the lumen thereof.

2. Description of the Prior Art

When inserting a venous catheter for total parenteral nutrition or an endotracheal tube, it is general practice to insert a metal wire or a stylet into a catheter to give some rigidity to the catheter or tube since such a catheter is too soft to insert into the blood vessel or trachea without causing bending of the catheter. The stylet is bent into a desired shape as occasion demands. For example, in case of intratracheal intubation, the stylet is bent into a shape corresponding to the shape of respiratory tract of a patient whose larynx being expanded.

In general, however, the stylet is of a metal such as stainless steel and has an acute-angled end. Thus, the stylet of the prior art has disadvantages that blood vessel walls or trachea walls may be injured by the distal end of the stylet protruded from the catheter during insertion of the catheter. Further, it is occasionally required to use the catheter filled with heparinized saline to perform priming operations. In such a case, it is necessary to remove the stylet from the catheter to fill the catheter with heparinized saline. In addition, it requires a great deal of skill to insert the stylet of the prior art into a correct position of the superior vena cava through the subclavian vein.

SUMMARY OF THE INVENTION

It is therefore an object of the present invention to provide a stylet assembly which is prevented from injuring blood vessels.

Another object of the present invention is to provide a stylet assembly which facilitates correct and safe insertion a catheter to a desired position with ease.

Still another object of the present invention is to provide a stylet connector which facilitates priming operations without removal of a stylet from a catheter.

According to the present invention, there is provided a stylet assembly comprising a stylet body and a connector for connecting the stylet to a catheter, said stylet body being composed of a piece of wire bent double and twisted together to form a rounded end serving as a distal end at one end, said connector having a stylet body connecting portion for holding a proximal end of said stylet body and means for fixedly holding the catheter to prevent the catheter from slipping from the stylet during use.

In a preferred embodiment, the stylet body is bent at a distal portion at a certain angle to allow the catheter to be correctly inserted into a desired place in the blood vessel. In this case, the connector may be provided with a certain mark indicating a bending direction of the stylet body.

According to the present invention, there is also provided a connector comprising a tubular body having at one end a stylet body connecting portion and at the other end an inflow port for medical solution, said stylet body connecting portion holding the stylet body and providing passages for flow of a medical solution from a lumen thereof without removal of the stylet when performing the priming operation.

The stylet connector further includes a sleeve rotatably mounted on the distal end of the tubular body to form a means for fixing a catheter. Preferably, the stylet body connecting portion is provided integrally and coaxially with the tubular body.

BRIEF DESCRIPTION OF THE DRAWINGS

These and other objects and features of the present invention will be explained in detail, making reference to the accompanying drawings which show one preferred embodiment of the present invention, and in which.

DETAILED DESCRIPTION OF THE PREFERRED EMBODIMENTS

Figure 1:
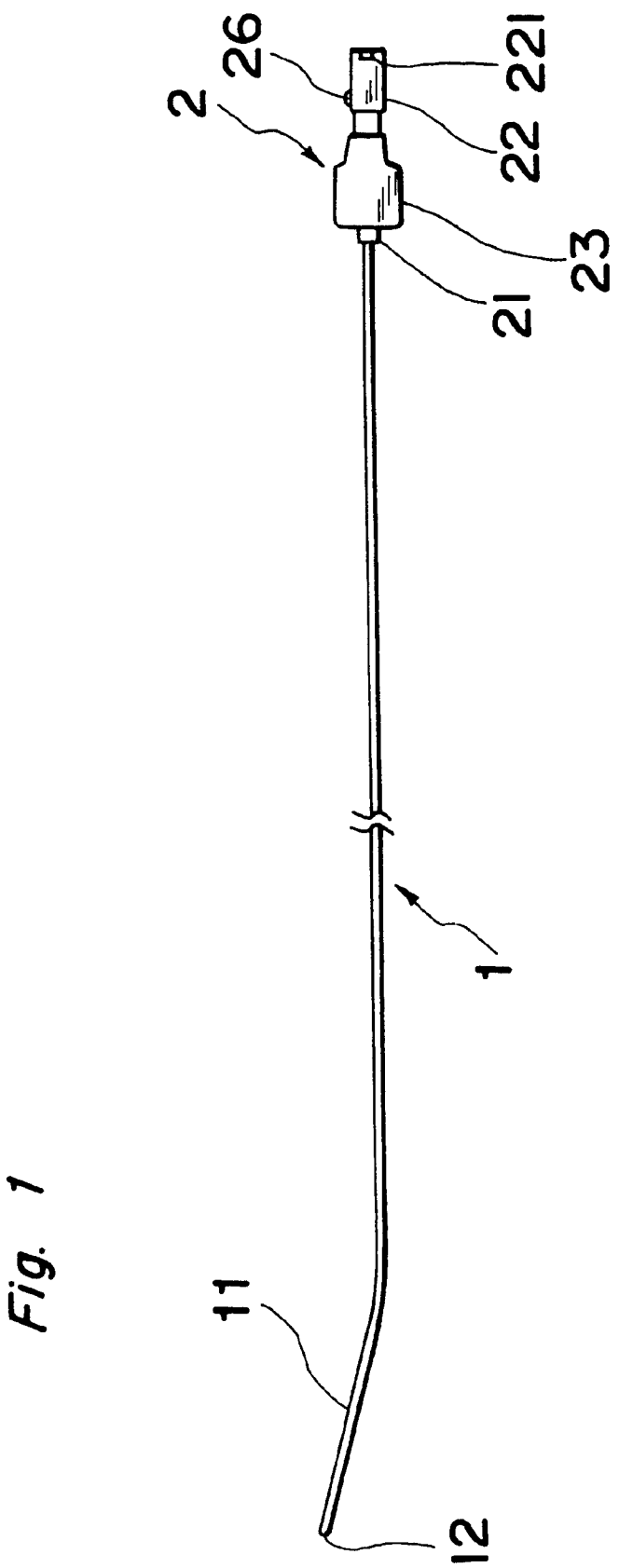
FIG. 1 is a plan view illustrating a stylet assembly according to the present invention.

Referring now to FIGS. 1, 3, 4 and 5 there is shown a stylet assembly S according to the present invention, which comprises a stylet body 1 and a stylet connector 2 for attachment of the stylet to a catheter. The stylet 1 is preferably bent at a certain angle at a certain position to form an angled, or offset distal end portion 11, though the stylet body 1 may be formed in a straight line. The connector 2 comprises a tubular member 20 having at one end a stylet body connecting portion 24 and at the other end an inflow port 25 for a liquid medicine. The connector 2 is provided with a sleeve 23 rotatably mounted on the tubular member 20 on the side of its distal end to form a means for fixing a catheter 3, as shown in FIG. 6. In use, the stylet body 1 is inserted into a lumen of the catheter 3 through a connector 31 of the catheter and then fixed to the catheter 3 by engagement of the connector 31 with the catheter-fixing means 23.

Figure 2:
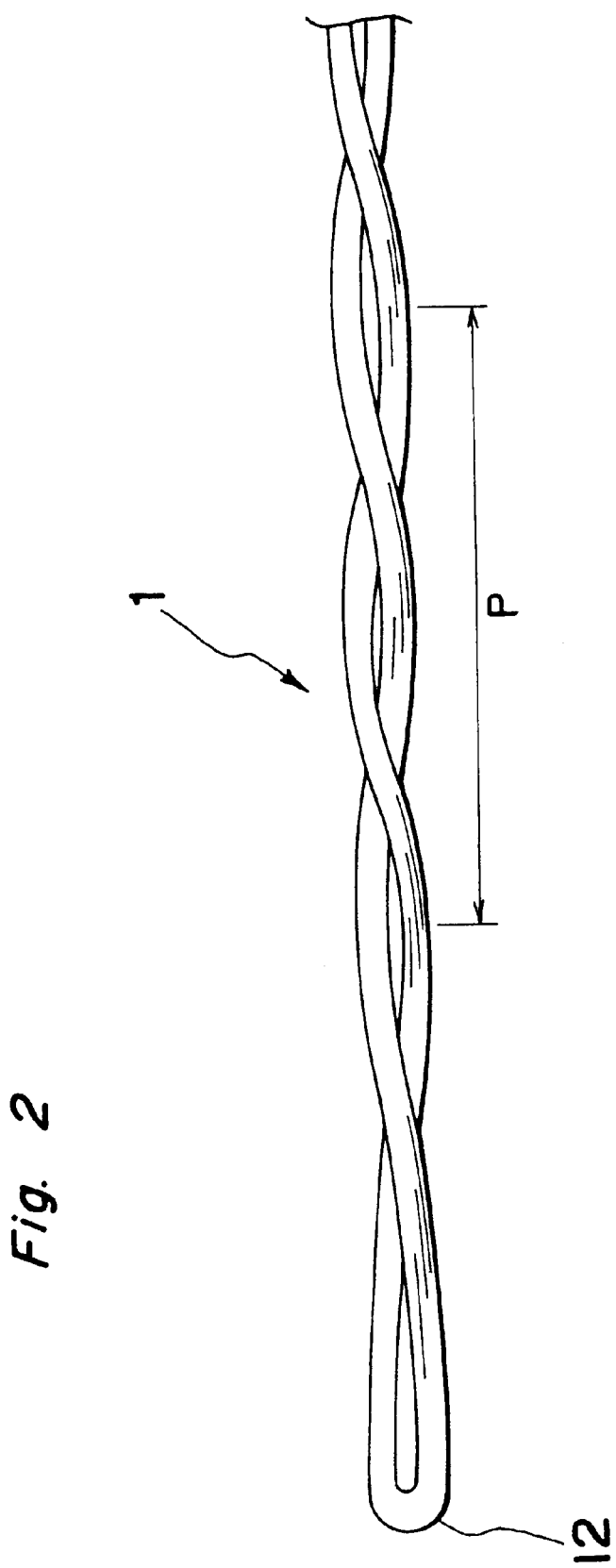
FIG. 2 is an enlarged view of a distal end of the stylet, or stylet body, shown in FIG. 1.

As best shown in FIG. 2, the stylet body 1 is composed of a piece of wire bent double and twisted together to form a hairpin or rounded end 12. This stylet body may be prepared, for example, by bending a piece of stainless steel wire double to form a rounded distal end 12 and then twisting the doubled wire together. The stylet body 1 is so attached to the connector 2 that the rounded end 12 becomes an distal end of the stylet body 1. The pitch P of the twisted wire varies with material and size of the wire. In case of a piece of stainless steel wire with a diameter of 0.2 mm, it is preferred to twist the wire at a pitch of 5 to 8 mm, preferably, 6 mm. Although the stylet body 1 may be used in a straight form, the stylet body 1 of this embodiment is bent at a certain position away from the distal end at a certain angle so that the catheter can be correctly inserted into a desired place in the blood vessel of a patient. The size of the stylet body 1 varies with its use. In case of a stylet for superior vena cava, the stylet body 1 preferably has a length 300 mm and is bent at an angle of 10° to 15° at a distance of 12 mm from the distal end 12.

The stylet connector 2 has the stylet body connecting portion 24 where a proximal end 13 of the stylet body 1 is fixed, and a means 23 for fixing the catheter 3. The connector 2 comprises of a tubular member 20 made of a metal such as stainless steel or a synthetic resin such as polypropylene, polyethylene, polyester, ABS resin or the like. A small-sized portion 21 of the connector 2 is luer-tapered as indicated by 21a to ensure engagement with a connector 31 of the catheter 3 having a female luer-tapered shape.

Figure 3:
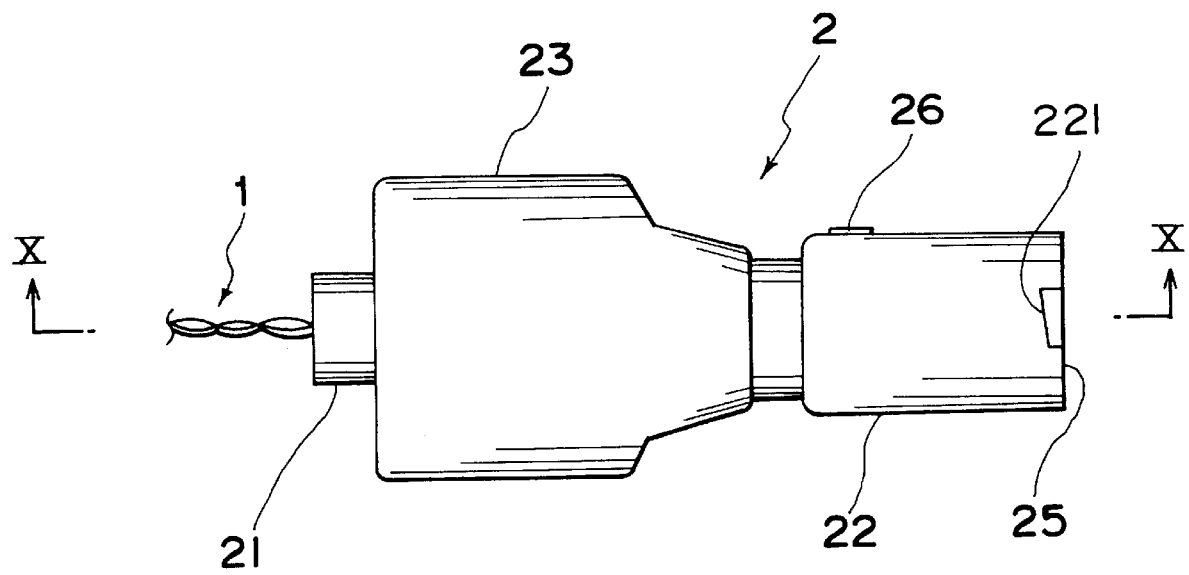
FIG. 3 is an enlarged view of a connector used in the stylet assembly of FIG. 1.
Figure 4:
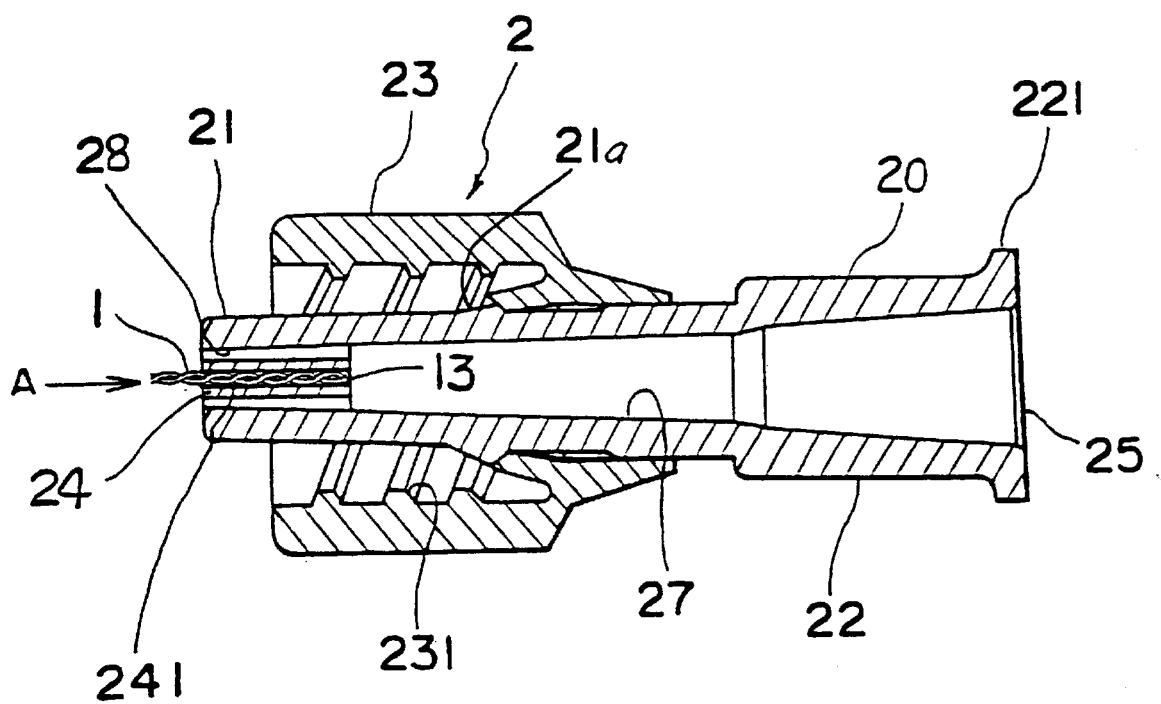
FIG. 4 is a sectional view taken along a line X—X in FIG. 3.
Figure 5:
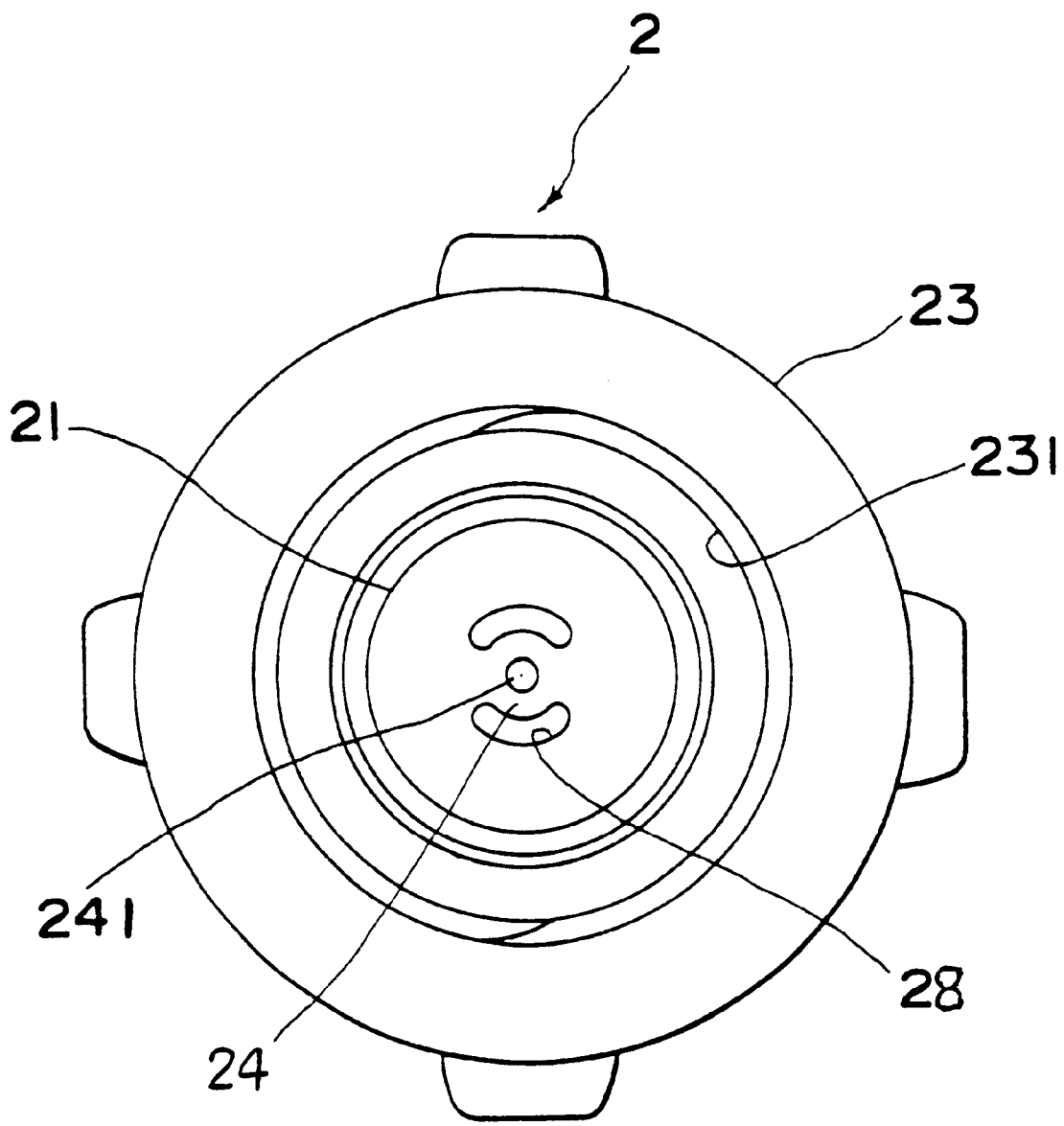
FIG. 5 is an enlarged side view of the connector taken from the direction of an arrow A shown in FIG. 4.
Figure 6:
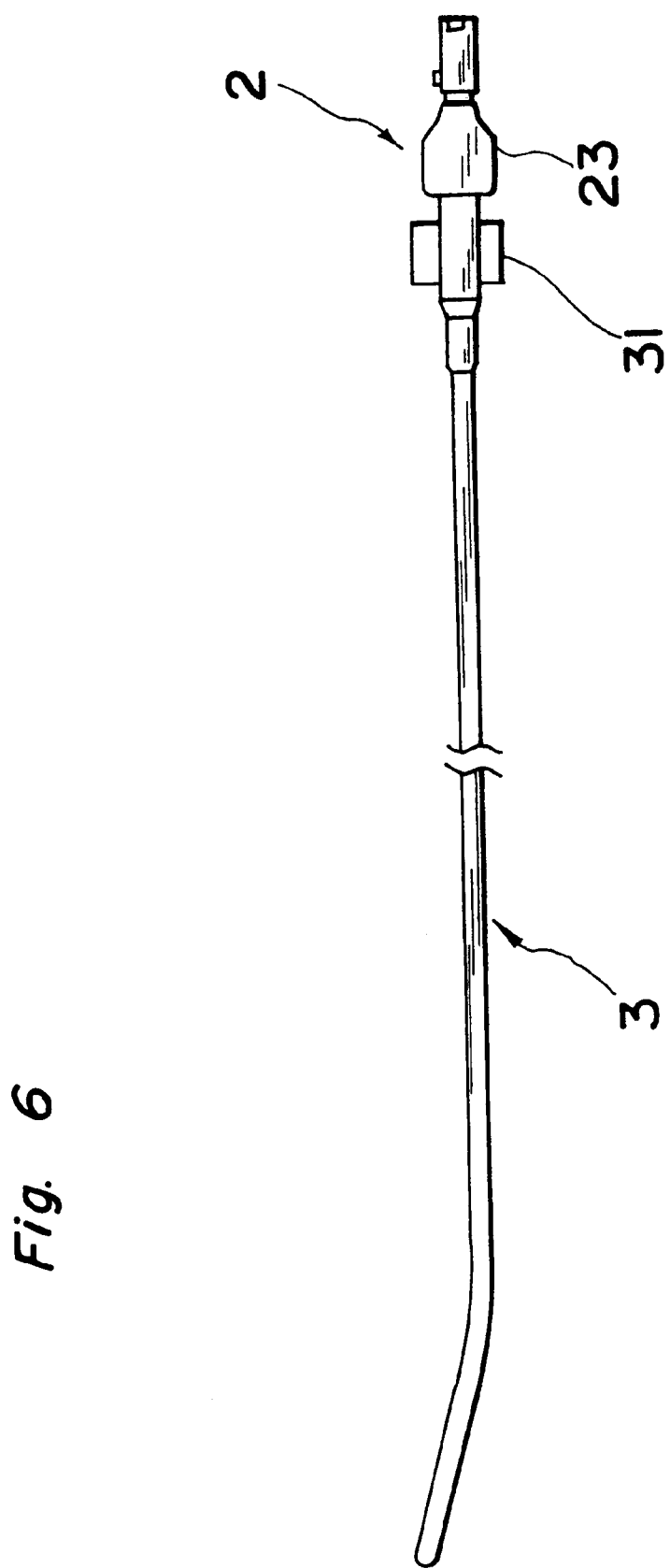
FIG. 6 is a plan view illustrating the stylet assembly of FIG. 1 with a catheter into which the stylet is inserted.

As shown in FIGS. 3 to 5, the stylet connector 2 has a tapered lumen 27, and the stylet body connecting portion 24 is provided integrally and coaxially with the tubular member 20 so as not to obstruct fluid paths 28. Thus, when performing priming procedures, a medical solution fed into the lumen of the stylet connector 2 is allowed to flow into the catheter 3 through the paths 28 without removal of the stylet S from the catheter 3. The stylet body connecting portion 24 has a through-hole 241 for insertion of the stylet body 1 coaxially with the axis of the tubular member.

A large-sized proximal portion 22 is provided with a medicine port 25 of a female luer-tapered shape and has double-start threads 221 close to the fluid port 25. A suitable injection means such as syringe (not illustrated in the drawings) can be connected to the fluid port 25 to inject a medical solution such as physiological saline or heparinized physiological saline into the catheter 3. The double-start thread is intended to connect a lock-type syringe or a lock connector such as lock-type three-way valve to the stylet. In order to make it easy to perform insertion of the catheter 3, the proximal portion 22 may be provided with a mark 26 indicating the bending direction of the distal end 11 of the stylet 1.

The sleeve 23 is slidably mounted on an outer wall of the tubular member on the side of the distal end of the connector 2 to prevent the catheter 3 connected to the connector 2 from falling away from the stylet. The sleeve 23 is movable in the direction parallel to the axial direction of the tubular member but is prevented from falling away from the tubular member. The inner wall of the sleeve 23 is provided with female threads 231 intended to engage with male engaging means (not shown in the drawings) such as double-start threads or male screw threads.

As explained above, the stylet assembly of the present invention has the following advantages: (1) The rounded distal end of the stylet enables to protect the blood vessel from injury by the protruded distal end of the stylet when inserting the stylet into the catheter; (2) if the stylet has a distal end bent at a certain angle, it is possible to correctly insert the catheter into the blood vessel with ease as the bent distal end minimizes mistakes during insertion of the stylet; (3) the connector with a medicine port makes it possible to perform priming operations without removal of the stylet being inserted in the catheter, to improve the procedures and to reduce time required for surgical operation; and (4) it is possible to avoid fear of secondary infection as the priming operation can be done without removal of stylet from the catheter.

What is claimed is:

1. A stylet assembly for use with a catheter, the stylet assembly comprising:
    a stylet body to be received within the catheter, the stylet body having a proximal end and a distal end and comprising a piece of wire bent double and twisted together to form a rounded end at the distal end thereof, the stylet body being bent adjacent the distal end thereof, forming an offset distal end portion for facilitating correct placement of the catheter into a desired place in a blood vessel; and
    a stylet connector for connecting the stylet assembly to the catheter, the stylet connector comprising (1) a tubular member having an inflow port at a proximal end thereof and a flow passage extending through the tubular member between the inflow port and a distal end of the tubular member, the tubular member also having at the distal end thereof a connecting portion including (1a) a central through-hole in which the proximal end of the stylet body is fixedly held and (1b) at least another flow passage within the tubular member around the central through-hole and the proximal end of the stylet body, whereby fluid introduced at the inflow port can flow through the tubular body and into a coupled catheter without removal of the stylet body and (2) means for coupling with the catheter to prevent a coupled catheter from separating from the stylet connector during use.

2. The stylet assembly according to claim 1, wherein the stylet connector carries a mark which affords an indication of the orientation of the offset distal end portion of the stylet body.

3. The stylet assembly according to claim 1, wherein the tubular member includes a first portion and a second portion integrally formed therewith, the second portion being smaller in cross-section than the first portion.

4. The stylet assembly according to claim 3, wherein the second portion of the tubular member is externally luer-tapered so as to engage with an internally luer-tapered connector of the catheter.

5. The stylet assembly according to claim 4, wherein the means for coupling with the catheter comprises a threaded sleeve rotatably carried on the tubular member.

6. The stylet assembly according to claim 1, wherein the means for coupling with the catheter comprises a threaded sleeve rotatably carried on the tubular member.

7. A connector for connecting a stylet assembly to a catheter, the connector comprising a tubular member and means on the tubular member for coupling with the catheter, and wherein:
    the means on the tubular member for coupling with the catheter comprises a threaded sleeve rotatably carried on the tubular member; and
    the tubular member includes (1) an inflow port provided at a proximal end of the tubular member, (2) a flow passage extending through the tubular member between the inflow port and a distal end of the tubular member and (3) a connecting portion, provided at the distal end of the tubular member, for fixedly holding a proximal end of the stylet body, the connecting portion defining at least another flow passage within the tubular member and about the proximal end of a stylet body held in the connecting portion, whereby, when performing a priming operation, fluid introduced at the inflow port can flow through the tubular body and into a connected catheter without removal of the stylet.

8. The connector according to claim 7, wherein the connecting portion is coaxially disposed within the tubular member.

* * * * *